US006572870B2

(12) United States Patent
Ribier et al.

(10) Patent No.: US 6,572,870 B2
(45) Date of Patent: Jun. 3, 2003

(54) ANHYDROUS COSMETIC MAKEUP COMPOSITION CONTAINING A FATTY PHASE

(75) Inventors: Alain Ribier, Paris (FR); Jean-Thierry Simmonet, Paris (FR); Dolores Miguel, Bourg la Reine (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/905,938

(22) Filed: Jul. 17, 2001

(65) Prior Publication Data

US 2001/0055601 A1 Dec. 27, 2001

Related U.S. Application Data

(63) Continuation of application No. 09/630,957, filed on Aug. 2, 2000, now Pat. No. 6,319,508, which is a continuation of application No. 07/954,362, filed on Sep. 29, 1992, now abandoned.

(30) Foreign Application Priority Data

Sep. 30, 1991  (FR) ............................................ 91 11985

(51) Int. Cl.[7] ................................................ A61K 9/00
(52) U.S. Cl. ........................ 424/401; 424/450; 424/64; 424/59; 424/70.7; 514/772; 514/785; 514/787; 514/844
(58) Field of Search ................................ 424/401, 450, 424/64, 59, 70.7; 514/772, 785, 787, 844

(56) References Cited

U.S. PATENT DOCUMENTS

| 3,641,239 | A | 2/1972 | Mohriok ...................... 424/64 |
| 3,662,011 | A | 5/1972 | Hindin et al. ............... 260/668 |
| 3,662,061 | A | 5/1972 | Lachampt et al. ............. 424/64 |
| 3,890,358 | A | 6/1975 | Hutchinson et al. ..... 260/410.6 |
| 3,957,969 | A | 5/1976 | Fujiyama et al. ............. 424/64 |
| 4,311,712 | A | 1/1982 | Evans et al. ................ 424/365 |
| 5,004,611 | A | 4/1991 | Leigh .......................... 424/450 |
| 5,053,217 | A | 10/1991 | Leigh .......................... 424/450 |
| 5,108,737 | A | 4/1992 | Dunphy et al. ............... 424/64 |
| 5,124,081 | A | 6/1992 | Vanlerbergh ................. 424/450 |
| 5,141,674 | A | 8/1992 | Leigh .......................... 252/305 |
| 5,141,751 | A | 8/1992 | Tomikawa ................... 424/450 |
| 5,151,272 | A | 9/1992 | Engstrom .................... 424/450 |
| 5,593,662 | A | 1/1997 | Deckner et al. ............. 424/401 |
| 5,855,876 | A | 1/1999 | Deckner et al. ............. 424/401 |
| 6,090,396 | A | 7/2000 | Deckner et al. ............. 424/401 |
| RE37,198 | E | 5/2001 | Ser ............................... 424/64 |
| 6,325,995 | B1 | 12/2001 | El-Nokaly et al. ............ 424/64 |

FOREIGN PATENT DOCUMENTS

| CA | A 1 292 62 | 12/1991 |
| EP | 0158441 | 10/1982 |
| EP | B10 087993 | 9/1983 |
| EP | A10 087993 | 9/1983 |
| EP | 0120722 | 10/1984 |
| EP | A-195575 | 9/1986 |
| EP | A-0 474 270 | 3/1992 |
| EP | A-0-524 892 | 1/1993 |
| EP | A-534823 | 3/1993 |
| EP | A-0545715 A1 | 6/1993 |
| EP | 0 660 696 B1 | 7/1995 |
| EP | 0660 697 B1 | 7/1995 |
| FR | 2390159 | 12/1978 |
| GB | A-1182173 | 3/1970 |
| GB | A-1 192 080 | 5/1970 |
| GB | 9108043.2 | 7/1993 |
| JP | 55-38332 | 3/1980 |
| JP | A-1143812 | 6/1989 |
| JP | A-55038332 | 4/1992 |
| LU | 54005 | 3/1969 |
| WO | WO-A-87/07502 | 12/1987 |
| WO | WO 87/07502 | 12/1987 |
| WO | WO-A-92/18103 | 10/1992 |
| WO | WO 92/18103 | 10/1992 |

OTHER PUBLICATIONS

Payne et al., "Proliposomes: A Novel Solution to an Old Problem", Journal of Pharmaceutical Sciences, vol. 75, No. 4, Apr. 1986, pp. 325–329.

Payne et al., "Characterization of Proliposomes", Journal of Pharmaceutical Sciences, vol. 75, No. 4, Apr. 1986, pp. 330–333.

Fukushima "Improved Oily Foundation Composition", Patent Abstracts of Japan, vol. 4, No. 73 (C–12)[552], May 1980, No. 55–38332(A).

French Search Report of FR 91 11985.

Decison of the Opposition Division (French & English text), EPO, dated Jan. 21, 2000, relating to Appln. No. 92402.3 (European Patent No. 0534823), which claims benefit of F 91 11985, which is the priority document for the present U.S. application.

Ingredient disclosure statement for Cover Girl Luminesse Lipsticks dated Nov. 4, 1986 (English text).

"Happi", Jan. 1998, p. 53.

(List continued on next page.)

Primary Examiner—Thurman K. Page
Assistant Examiner—Lakshmi Channavajjala
(74) Attorney, Agent, or Firm—Nixon & Vanderhye, P.C.

(57) ABSTRACT

An anhydrous cosmetic makeup composition contains in addition to a fatty phase formed from oils, fatty bodies and surfactants, and optionally waxes, a vesicular lipidic phase that contains at least one ionic or nonionic amphiphilic lipid and optionally additives. The anhydrous composition also preferably contains at least one cosmetically and/or dermopharmaceutically active material. In the presence of an aqueous phase these compositions release vesicles of the vesicular lipidic phase and potentialize the activity of the cosmetically and/or dermopharmaceutically active material of the composition.

127 Claims, No Drawings

OTHER PUBLICATIONS

Two articles from Journal of Pharmaceutical Sciences, 1986.
A copy of Proctor & Gamble Company's Request of the Board of Appeal of the EPO to over turn the Opposition Division's Decision concerning grant of European Patent No. 0534823 (undated, English text).
Affidavit of David Walling executed May 31, 2000, 3 pages including attached Figures A (1 page), B (1 page, color) and C (2 pages, color).
L'Oreal Response to Appeal of Proctor & Gamble Company Appeal concerning grant of European Patent No. 0534823 (French & English text) dated Feb. 9, 2001 including Figures T1–T7.
Declaration of Pascal Arnaud (French and English text) (Declaration 1 executed Feb. 8, 2001).
Declaration of Jean–Thierry Simonnett (French and English text) (Declaration 2 executed Feb. 8, 2001 and containing 7 pages of figures).
U.S. Patent Appln. Ser. No. 08/115,093 filed Sep. 7, 1993, El–Nokaly et al.
U.S. Patent Appln. Ser. No. 08/066,351 filed May 21, 1993, El–Nokaly et al.
U.S. Patent Appln. Ser. No. 07/947,692 filed Sep. 21, 1992, El–Nokaly et al.
Copy of Communication under Rule 51(4) EPC dated Mar. 26, 1996, with regard to EP Application No. 93921577.8–2114; The Proctor & Gamble Company.
Opposition paper dated Oct. 8, 1997, with regard to European Appln. No. 0660696 (English text).
Opposition paper dated Oct. 8, 1997, of L'Oreal with regard to European Application No. 660696 (French & English text).
English translation of JP 55–38332 (i.e., (26) and document D12 listed in (40 below).
Communication from the EPO, EPO Form 2318 11.92 dated Nov. 13, 1997 with regard to Opposition of Application No. 93921577.8–2114 (European Patent No. 0660696).
Copy of EPO Form 2911 10.93 dated Mar. 31, 1998 with regard opposition of Application No. 93921577.8–2114 (European Patent No. 0660696).
Copy of Statutory Declaration of Magda El–Nokaly executed May 18, 1998 and submitted in connection with Opposition of European Patent No. 0 660 696.
Observations in Support of Patent in Suit, submitted in opposition of European Patent No. 0660696 (undated but signed by Maura O'Connell).
Letter of May 22, 1998, to the European Patent Office signed by Maura O'Connell in Opposition of European Patent No. 0660696.
Copy of Statutory Declaration document M12.06.98 executed May 18, 1998, by Magda El–Nokaly filed in Opposition of European Patent No. 0660696.
Letter dated Jun. 8, 1998, executed by Maura O'Connell to the European Patent Office with regard to Opposition of European Patent No. 0660696.
Letter of Oct. 6, 1998, executed by Catherine Lhoste with regard to Opposition of European Patent No. 660696 (French & English text).
Copy of letter dated Feb. 3, 1999, executed by Catherine Lhoste with regard to Opposition of European Patent No. 660696 (French text).
Copy of letter dated Nov. 5, 1999, executed by Odile Bredeville to European Patent Office with regard to Opposition of European Patent No. 660696 (French & English text).
Copy of letter dated Dec. 2, 1999, executed by Odile Bredeville to European Patent Office with regard to Opposition of European Patent No. 660696 (French & English text).
Copy of Brief Communication from European Patent Office regarding Summons to Attend the Oral Proceedings with regard to Opposition of European Patent No. 0660696 dated Nov. 8, 1999.
Copy of Summons to Attend the Oral Proceedings dated May 4, 1999, from the European Patent Office with regard to Opposition of European Patent No. 0660696.
"The Lipid Handbook", Chapman & Hall, second edition (1994) p. 443–446 (document D2 listed in (40)).
Lutton, E.S., J. Am. Oil Chem. Soc., 42 (1966) p. 1068–1070 (document D3 listed in (40)).
Product sheet for Hostaphat KO 300 N (document D5 from (40) French text).
Declaration from M. Simonnet and phase contrast images dated Sep. 26, 1997.
Cosmetic Research Int. 3 (1991) p. 37.
"Handbook of surfactantas", Chapman and Hall (1991) p. 33–34.
"Cosmetics & Toiletries", vol. 106 (1991) p. 69–72.
"International Cosmetic Ingredient Distionary and Handbook" CTFA, seventh ed (1997) vol. 1, p. 819.
"Cosmetics, Science and Technology", 1992, vol. 1, p. 27 and 34.
"CTFA Cosmetic Ingredient Dictionary", third ed. (1982) p. 325.
"International Cosmetic Ingredient Dictionary", fifth ed. (1993) p. 760.
Declaration 3 from P. Hallegot, dated Jan. 26, 1999 (French & English text).
Copy of letter dated Feb. 3, 1999 executed by Catherine Lhoste with regard to Oppostiion of European Patent No. 660696 (French & English text).
Copy of Declaration 1 of P. Arnaud dated Jan. 20, 1999 (French & English text).
Copy of Declaration 2 of Jean–Thierry Simonnet dated Jan. 25, 1999 (French & English text).
Copy of minutes in accordance with Rule 76(4) EPC dated Dec. 23, 1999 in Opposition of EP Aplication No. 93921577.8–2114.
Copy of Description of EP 0 660 696 B1.
Copy of Interlocutory decision in Opposition proceedings (Article 106(3) EPC) dated Dec. 23, 1999 from European Patent Office, with regard to Opposition of European Patent No. 0660696.
Copy of Articles 106, 107, 108 from the European Patent Office.
Copy of $1^{st}$ Auxilliary Request, Claims with regard to the Opposition of European Patent 0660696.
Copy of Notice from the European Patent Office signed by Maryse Dainese and dated Mar., 2000 regarding the Appeal in European Patent No. 0660696.
Copy of letter dated Feb. 22, 2000, signed by Odile Bredeville regarding the Opposition of European Patent No. 660696 (French text).

Copy of letter dated Apr. 21, 2000, signed by Odile Bredeville regarding the Opposition in European Patent No. 660696 (French & English text).

Copy of International Search Report in EP 0524 892A, Sep. 16, 1992.

Copy of letter of May 27, 1998 from Mrs. Lhoste to EPO regarding Patent No. 660697 (French & English text).

EPO Communication Pursuant to Rule 57(2) dated Aug. 3, 1998 re: Opposition to EP 0660697.

Brief Communication of EPO dated Feb. 19, 1999 re: Opposition to EP 0660697 with letter of Maura O'Connell dated Feb. 9, 1999 to EPO.

Copy of letter dated Jun. 22, 1999 of Mrs. Lhoste to EPO re: Opposition to EP 660697 (French & English text).

Summons to Attend Oral Proceedings Pursuant to Rule 71(1) EPC in Opposition to EP 660697 dated Jul. 27, 2000 with copy of Preparation of Oral Proceedings dated Jul. 6, 2000.

Copy of letter to EPO dated Nov. 14, 2000 from Mrs. F. Bulle re: Opposition to EP 660697 with attached Declaration of Jean–Claude SER executed Nov. 13, 2000 and attached color Figure (French & English text).

Copy of letter to EPO dated Nov. 17, 2000 from H.S. Griffiths re: Opposition to EP 660697.

Brief Communication from EPO dated Nov. 13, 2000 with copy of Nov. 1, 2000 letter from H.S. Griffiths to EPO re: Opposition to EP 660697.

Brief Communication from EPO dated Nov. 17, 2000 with attached copy of Nov. 14, 2000 letter of Maura O'Connell to EPO.

Claims of First Auxilliary Request, Second Auxilliary Request, Third Auxilliary Request, Fourth Auxilliary Request, Replacement Main Request, Replacement Auxilliary Request, Replacement Second Auxilliary Request, and Replacement Third Auxilliary Request in Opposition to EP 660697, and copy of Decision of Jun. 21, 1994 in T0565/981—3.3.3 of Board of Appeal of the EPO.

Brief Communication of EPO dated Apr. 19, 2001 to Mrs. F. Bulle with attached letter of Apr. 6, 2001 from Maura O'Connell to EPO re: Opposition of EP 660697.

Decision revoking th European Patent (Article 102(1), (3) EPC)—EP 660697 dated Apr. 19, 2001.

Appeal notice of Maura O'Connell to EPO dated Jun. 21, 2001 re: Opposition of EP 660697.

EPO Board Appeal notice dated Jun. 29, 2001 to Mrs. F. Bulle re: Opposition of EP 660697.

EPO Board of Appeal letter and Article 108 Communication dated Sep. 13, 2001 re: Opposition to EP 660697.

Decision of the Technical Board of Appeal 3.3.7 of Dec. 17, 2001 re: Opposition of EP 660697.

Cosmetics Science and Technology, $2^{nd}$ Ed., vol. 1, Wiley Interscience, 1972, Chapter 12, p. 365–392, Lauffer, Chapter 12 "Lipsticks".

The Chemistry and Manufacture of Cosmetics, $2^2$ Ed. vol. IV, 1975, Chapter 44, pp. 767–840, deNavarre, "Lipstick".

English translation of JP–A–1 1439812.

Declaration of Jean–Thierry Simonnet executed Apr. 7, 2000 (marked "Annex D36" (French text) (English translation attached)).

Declaration of Philippe Hallegot executed Apr. 12, 2000 (marked "Annex D37" (French text) (English translation attached).

Declaration of Jean–Pierre Lechaire executed Apr. 13, 2000 (marked "Annex D38" (French text) (English translation attached).

Cosmetics Science and Technology, $2^{nd}$ Ed., vol. 1, Wiley Interscience, 1972, Chapter 12, p. 365–392, Lauffer, Chapter 12 "Lipsticks" (document "(9)") in (85) above).

Declaration of Pascal Arnaud executed Apr. 7, 2000 (marked "Annex D35" (French text) (English translation attached).

English translation and Japanese text of JP–A–55038332 (document "(4)" in (85) above).

ANHYDROUS COSMETIC MAKEUP COMPOSITION CONTAINING A FATTY PHASE

This application is a continuation of application Ser. No. 09/630,957, filed Aug. 2, 2000, now U.S. Pat. No. 6,319,508, which in turn is a continuation of application Ser. No. 07/954,362, filed Sep. 29, 1992, now abandoned entire content of which is hereby incorporated by reference in this application.

The present invention relates to anhydrous cosmetic makeup compositions comprising a fatty phase and a cosmetic treatment process using these compositions.

Known anhydrous cosmetic compositions comprise a fatty phase containing mineral or organic oils, fatty bodies, surfactants intended to provide a homogeneous phase and, most often, waxes. Dyes and pigments are added when it is desired that the anhydrous composition be colored.

Anhydrous cosmetic makeup compositions, such as a lip rouge, an eyelid shadow, a molded complexion foundation, and a molded cheek rouge, have as a principal purpose the application of dyes and pigments to the skin, in an even, homogeneous and durable manner.

Moreover it is known to employ cosmetic and/or dermopharmaceutical compositions which function to treat the skin on topical application thereto.

The exigencies of modern life have necessitated efforts to simplify cosmetic treatments by using cosmetic compositions having several functions thereby reducing the number of required cosmetic treatment operations.

These efforts have involved the introduction in the anhydrous makeup compositions of cosmetic and/or dermopharmaceutical active materials. To this end, efforts have been made to introduce lipophilic active materials which can be dissolved in the fatty phase of the anhydrous compositions. This fatty phase often contains a large amount of wax and its absorption by the skin or the mucous membrane is very limited. Consequently, the effectiveness of the active materials, which is a function of the penetration of the fatty phase in the skin, is also quite limited.

Consideration has also been given to introducing water-soluble active materials. However, their introduction requires costly technological measures such as the lyophilization of the active materials, then their microdispersion in the fatty phase or the incorporation of the active materials in solid supports such as microspheres or microcapsules and then their dispersion in the fatty phase. In this latter case, the amount of active material that can be introduced is limited because the incorporation of solid supports, containing the active materials, modifies in a significant manner the mechanical properties of the anhydrous compositions.

Thus, until now, the problem of introducing cosmetic and/or dermopharmaceutical active materials into anhydrous cosmetic compositions has not been resolved in a satisfactory manner.

This problem also exists in the case of anhydrous cosmetic products such as deodorant sticks and anhydrous anti-circle compositions.

On the other hand, it is known that certain ionic or non-ionic amphiphilic lipids and certain mixtures of amphiphilic lipids are capable, on contact with an aqueous phase, of forming vesicles constituted by more or less spherical lamina of the vesicular lipidic phase, encapsulating an aqueous phase.

In a known manner additives can be introduced into the vesicular lipidic phase to improve the stability and the permeability of the resulting vesicles. These additives can be sterols, and in particular, cholesterol or dicetylphosphate.

In the present application and in the claims, the term "provesicular lipidic phase" designates amphiphilic lipids capable of forming vesicles, mixtures of ionic and/or non-ionic amphiphilic lipids capable of forming vesicles and amphiphilic lipids or mixtures of amphiphilic lipids containing additives to improve the stability and permeability of the resulting vesicles.

It is well known that these vesicles already possess, in themselves, a cosmetic activity on topical application but especially that they permit the encapsulation of water-soluble and liposoluble cosmetic and/or dermopharmaceutical active materials in the lipidic and/or aqueous phase. The preparation of vesicles from amphiphilic lipids and their use in cosmetics are, for example, described in French application 2,315,991.

Moreover it is known from FR A 2,416,008, that the lipidic vesicles can be lyophilized and that after lyophilization these vesicles retain their treating characteristics. From this one conclusion would be to introduce lyophilized liposomes and/or niosomes into anhydrous cosmetic makeup compositions. But this operation is complicated and costly on the industrial level, for it requires producing vesicles from amphiphilic lipids, lyophilizing them in the presence of anti-agglomerating agents and/or cyroprotectors having no particular advantage for cosmetic compositions, and then to incorporate them at an elevated temperature in a complex cosmetic product containing melted oils and waxes.

According to the present invention the applicants have found that the provesicular lipidic phase, capable of forming vesicles in the presence of water, retains its ability to form vesicles when it is mixed with a fatty phase, generally employed for the production of anhydrous cosmetic compositions, which fatty phase contains organic and/or mineral oils, fatty bodies, and most often, waxes and surfactants.

In effect, as shown in the comparative examples given below, that after contact with water, the formation of vesicles in the aqueous phase of satisfactory quality and significant quantity is observed. Moreover, it is noted that the resulting vesicles retain their capacity to encapsulate hydrophilic and/or lipophilic active materials and that under these circumstances the effectiveness of the active material, introduced into the anhydrous composition, is very clearly improved.

It was not obvious to the skilled artisan that when the provesicular lipidic phase, capable of forming vesicles in the presence of water, was mixed with the fatty phase, employed in the production of anhydrous cosmetic makeup compositions, it would again be possible by mere contact with an aqueous phase, to form vesicles therein. In particular, it was feared that, when the provesicular lipidic phase which is constituted of a mixture of ionic amphiphilic lipids and/or non-ionic amphiphilic lipids or amphiphilic lipids combined with one or more additives, the combination of these different compounds, which can be required for the formation of vesicles in a stable form, would be destroyed by the oils, fatty bodies, waxes and the surfactants contained in the fatty phase of the anhydrous cosmetic product.

According to the present invention this discovery is utilized in the production of anhydrous cosmetic compositions containing in the fatty phase, a provesicular phase capable of forming vesicles on contact with water, these anhydrous cosmetic compositions being contacted with an aqueous phase at the time of their use to cause the formation of vesicles.

It is necessary to note that the contact with an aqueous phase is most often inherent in the method of application of these anhydrous cosmetic compositions.

For example, lip rouges are contacted with the labial mucous membrane, which is rich in water, and which is regularly moistened by the saliva; molded complexion foundations, eyelid shadows or cheek rouges are often hydrated just before application using a wet sponge; deodorant sticks are applied to the skin which is moistened by sweat secretions.

The present invention thus-relates to an anhydrous cosmetic composition comprising a fatty phase which is characterized by the fact that the fatty phase contains a provesicular lipidic phase containing at least one amphiphilic lipid capable of forming vesicles on contact with an aqueous phase.

Preferably, the cosmetic composition contains a water-soluble and/or liposoluble cosmetic and/or dermopharmaceutical active material.

The amount of the provesicular lipidic phase containing the amphiphilic lipids can represent from 0.1 to 30 percent by weight of the anhydrous composition, preferably from 1 to 20 percent.

In the provesicular lipidic phase, the amphiphilic lipids employed can be any amphiphilic lipid known for the production of vesicles in the presence of water. These lipids are, in a known manner, amphiphilic lipids of natural or synthetic origin, ionic or nonionic, having, per molecule, one or more long chain, saturated or unsaturated, linear or branched hydrocarbon chains, having preferably 8 to 30 carbon atoms. These chains are, for example, oleic, lanolic, tetradecylic, hexadecylic, isostearylic, lauric or alkyl phenyl chains, and one or more hydrophilic groups taken from hydroxyl, etheroxide, carboxyl, phosphate and amine groups.

Preferable ionic amphiphilic lipids include natural phospholipids (for example, egg lecithin or soy lecithin or sphingomyelin), synthetic phospholipids (for example, dipalmitoylphosphatidylcholine or hydrogenated lecithin). Amphoteric lipids having two lipophilic chains or a combination of two organic ions having a long chain of opposite signs can also be employed, as can anionic lipids.

Among the ionic amphiphilic lipids mention can be made of those which are described in Luxembourg patent application 85 971, filed on Jun. 23, 1985, and which are represented by the formula:

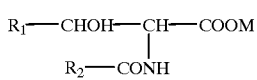 (I)

wherein $R_1$ represents $C_7$–$C_{21}$ alkyl or alkenyl, $R_2$ represents a $C_7$–$C_{31}$ saturated or unsaturated hydrocarbon radical, and M represents H, Na, K, $NH_4$ or a substituted ammonium ion derived from an amine and, principally a hydroxylated amine.

Preferable nonionic amphiphilic lipids include those containing, as hydrophilic groups, polyoxyethylenated or polyglycerolated groups, or groups derived from esters of polyols oxyethylenated or not, or even hydroxyamide derivatives. Advantageously, the nonionic amphiphilic lipids are selected from the group consisting of:

(1) linear or branched polyglycerol derivatives having the formula

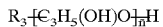 (II)

wherein

—$C_3H_5(OH)O$— is represented by the following structures taken separately or in admixture:

—$CH_2$—$CHOH$—$CH_2O$—,

and

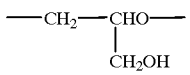

$\overline{n}$ has a statistical average value ranging from 1 to 6, $R_3$ represents:

(a) a linear or branched, saturated or unsaturated aliphatic chain containing from 12 to 30 carbon atoms; or hydrocarbon radicals of lanolin alcohols;

(b) $R_4CO$ wherein $R_4$ is a linear or branched aliphatic radical containing 11 to 29 carbon atoms; and (c) $R_5$—[$OC_2H_3(R_6)$—]—wherein $R_5$ has the meaning (a) or (b) given for $R_3$; —$OC_2H_3(R_6)$— is represented by the following structures taken separately or in admixture:

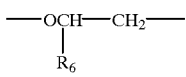

and

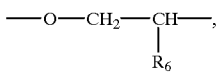

wherein $R_6$ has the meaning (a) given above for $R_3$, (2) polyglycerol ethers, linear or branched, having two fatty chains;

(3) polyoxyethylenated fatty alcohols;

(4) polyoxyethylenated sterols and phytosterols;

(5) ethers of polyols;

(6) esters of polyols oxyethylenated or not and, in particular, esters of polyoxyethylenated sorbitol;

(7) glycolipids of natural or synthetic origin, for example the cerebrosides;

(8) polyglycerolated α-diols;

(9) hydroxyamides represented by the formula:

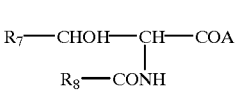 (III)

wherein $R_7$ represents a $C_7$–$C_{21}$ alkyl or alkenyl radical, $R_8$ represents a saturated or unsaturated $C_7$–$C_{31}$ hydrocarbon radical;

COA represents one of the following two groups:

(a)

wherein B is a mono or polyhydroxylated alkyl derived from a primary or secondary amine and $R_9$ represents hydrogen, methyl, ethyl or hydroxyethyl, and (b) COOZ wherein Z represents the residue of a $C_3$–$C_7$ polyol; and

(10) the ethers and esters described in French patent application 90 13139 filed on Nov. 14, 1990 and having the formula

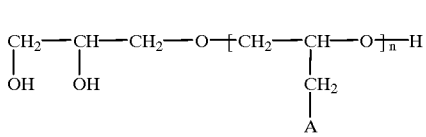

wherein

A represents —OR or

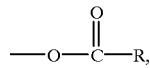

wherein R represents a saturated or unsaturated hydrocarbon radical, and n is 2 or has a statistical average value $\bar{n}$ greater than 1 and at most 6.

Preferably R represents a $C_7$–$C_{22}$ linear alkyl, a $C_7$–$C_{36}$ branched alkyl, a $C_{18}$ alkenyl or alkylaryl having a linear or branched $C_7$–$C_{16}$ alkyl chain. In the alkyl aryl radical, the aryl group is, preferably, phenyl. The alkenyl radical advantageously is an octadecene-9 yl or an octadecanediene-9,12 yl group.

In a known manner, various additives can be combined with the amphiphilic lipids to modify their stability and permeability. In this regard mention can be made of the optional addition of long chain alcohols and diols; sterols such as, for example, cholesterol and β-sitosterol; long chain amines and their quaternary ammonium derivatives; hydroxyalkylamines; polyoxyethylenated fatty amines; esters of long chain aminoalcohols, their salts and quaternary ammonium derivatives; phosphoric esters of fatty alcohols in free or neutralized form such as, for example, sodium dicetylphosphate and alkyl sulfates such as, for example, sodium cetyl sulfate; ionic derivatives of sterols; and certain polymers such as polypeptides and proteins.

As explained above, in accordance with the invention, there can be introduced into the fatty phase, cosmetic and/or dermopharmaceutical active materials. According to the present invention, only active materials known to have a cosmetic and/or dermopharmaceutical activity on topical application and capable of being encapsulated in amphiphilic lipid vesicles can be employed.

Representative lipophilic active materials include, principally, vitamin E, esters of vitamin E, polyunsaturated fatty acids, vitamin F, sunscreen agents, antioxidants, preservatives, vitamin A, retinoic acid and its esters.

Representative water-soluble active materials include, preferably, those which permit, on admixture with the provesicular lipidic phase the production of anhydrous lamellar phases, such as glycerol, sorbitol and other polyols having a close structure. Also useful are amino acids such as arginine, lysine, proline and serine; vitamins such as D,L-panthenol; and sunscreen agents.

In a known manner the fatty phase comprises fatty bodies such as cocoa butter and oils. Representative oils capable of being employed in accordance with the invention include, particularly:

mineral oils such as paraffin oil, petrolatum oil and oils having a boiling point between 310 and 410° C., oils of animal origin, such as perhydrosqualene, vegetable oils such as sweet almond oil, calophyllum oil, palm oil, avocado oil, jojoba oil, olive oil, ricin oil and cereal germ oils, such as wheat germ oil, silicone oils such as dimethylpolysiloxane, synthetic esters such as purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate and di-isopropyl adipate, organic alcohols such as oleic alcohol, linoleic alcohol, lanolenic alcohol, isostearyl alcohol and octyl dodecanol, and esters derived from lanolic acid such as isopropyl lanolate and isocetyl lanolate.

Other oils that can also be employed include acetyl glycerides, the octanoates and decanoates of alcohols and polyalcohols, such as those of glycol and glycerol, ricinoleates of alcohols and polyalcohols such as those of cetyl.

Most often waxes are also employed and representative waxes, employed in the present invention, include:

mineral waxes such as microcrystalline waxes, paraffin waxes and petrolatum waxes, fossil waxes such as ozokerite, montan wax, waxes of animal origin such as beeswax, spermaceti, lanolin wax, derivatives of lanolin such as lanolin alcohols, hydrogenated lanolin, hydroxylated lanolin, acetylated lanolin, lanolin fatty acids, and acetylated lanolin alcohol, waxes of vegetable origin such as candelilla wax, Carnauba wax, and Japan wax, hydrogenated oils, solid at 25° C., such as hydrogenated ricin oil, hydrogenated palm oil, hydrogenated tallow and hydrogenated cocoa oil, fatty esters, solid at 25° C., such as propylene glycol monomyristate and myristyl myristate.

Among other waxes, mention can be made of cetyl alcohol, stearyl alcohol, mono-, di- and triglycerides solid at 25° C., stearic monoethanol amide, colophane and its derivatives such as glycol and glycerol abietates, sucroglycerides and the oleates, myristates, lanolates, stearates and dihydroxystearates of calcium, magnesium, zinc and aluminum.

Pigments are introduced when the cosmetic composition must be colored.

Generally there are also added surfactant agents such as succinylglycerides, alkylphosphates, esters of fatty acids such as polysorbates sold under the trade name "TWEEN" by ICI Americas and esters of polyethyleneglycol such as those sold under the name "BRIJ", by ICI.

The anhydrous cosmetic composition, according to the invention, is prepared by mixing the various components. Preferably, the materials constituting the fatty phase and the materials constituting the provesicular lipidic phase are mixed separately. Then the resulting two phases are mixed until a homogeneous preparation is obtained. In this latter case the cosmetic and/or dermopharmaceutical active materials are preferably introduced into the-provesicular lipidic phase.

The present invention also relates to a process for the cosmetic treatment of the skin characterized by the fact that the anhydrous cosmetic composition, described above, is applied to the skin, the cosmetic composition being in contact with an aqueous phase when it is applied to the skin.

According to the invention, the contact of the anhydrous cosmetic composition with an aqueous phase can be effected just before application of the composition onto the skin. In this situation the composition can be removed with a wet sponge and the composition is spread on the skin using this sponge.

Contact can also be effected by spreading the composition on skin previously moistened either with saliva or perspiration, or by the water contained in the mucous membranes, or using an aqueous phase derived from an external source.

Contact can also be effected after application of the anhydrous cosmetic substance. In this case also, the aqueous phase can be constituted by perspiration or saliva or provided from an external source.

The objectives, characteristics an advantages of the present invention will appear more clearly from the examples given below as an illustration and without any limitation.

EXAMPLE 1

Comparison (1) Preparation of a fatty phase a having the following composition

| Polybutene | 5.04 g |
|---|---|
| Lanolin oil | 20.38 g |
| Octoxy glyceryl behenate | 20.38 g |
| Stearyl heptanoate | 9.84 g |
| Jojoba oil | 9.84 g |
| Ricin oil | 19.20 g |
| Butylhydroxytoluene | 0.06 g |
| Butylhydroxyanisole | 0.06 g |
| Microcrystalline wax | 7.60 g |
| Polyethylene 500 | 70.60 g |

The mixture of the various compounds above is effected at a temperature between 100 and 120° C. with stirring, using a bar magnet, until a well homogenized preparation is produced.

(2) Starting with this Fatty Phase A the Following Various Compositions are Prepared:

Composition A1: (not containing a provesicular lipidic phase but containing a liposoluble active material)

1% of α-tocopherol acetate, which is a liposoluble active material is mixed with 99% of the fatty phase A defined above.

Composition A2: (containing a nonionic provesicular lipidic phase but no liposoluble active material)

(a) A provesicular lipidic phase having the following composition is prepared by comelting at 100° C. under nitrogen: a nonionic amphiphilic lipid having the formula

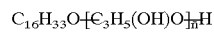   (V)

wherein

—C$_3$H$_5$(OH)O— is represented by the following structures, taken in admixture or separately:

—CH$_2$—CHO—   and   —CH—CH$_2$O—;   and
       |                   |
      CH$_2$OH           CH$_2$OH

| $\overline{n}$ has a statistical average value equal to 3 | 4.75 g |
|---|---|
| cholesterol | 4.75 g |
| dicetyl phosphate | 0.5 g |

(b) composition A2 is prepared by mixing 90% of fatty phase A and 10% of the above-described provesicular lipidic phase.

Composition A3: (containing a nonionic provesicular lipidic phase and containing a liposoluble active material)

(a) A provesicular lipidic phase having the following composition is prepared by comelting at 100° C. under nitrogen:

| nonionic amphiphilic lipid having formula V | 4.75 g |
|---|---|
| cholesterol | 4.75 g |
| dicetyl phosphate | 0.5 g |
| α-tocopherol acetate | 1 g |

(b) Composition A3 is prepared by mixing 89% of the above fatty phase A with 11% of the above-described provesicular lipidic phase. Composition A3 then contains 1% of α-tocopherol acetate.

Composition A4: (containing an ionic provesicular lipidic phase and not containing a liposoluble active material)

Employing the same process as that used for producing composition A3, a composition A4 is prepared and comprises:

90 weight percent of fatty phase A 10 percent of a vesicular lipidic phase constituted of 6% of soy lecithin sold under the trade name "LECINOL S 10" by Nikko, and 4% of phytosterol oxyethylenated with 5 moles of ethylene oxide, sold under the trade name "GENEROL 122 E5" by Henkel.

Composition A5: (containing an ionic provesicular lipidic phase and a liposoluble active material)

Using the same process as that employed in producing composition A1, composition A5 is prepared and consists of 89% of fatty phase A and 11% of a provesicular lipidic phase consisting of 6% of "LECINOL S10", 4% of phytosterol oxyethylenated with 5 moles of ethylene oxide sold under the trade name "GENEROL 122 E5" by Henkel and 1% of α-tocopherol acetate.

(3) Comparative Tests

A 1 g film of each of compositions A, A1, A2, A3, A4 and A5 is deposited in a Petri dish and then covered with 10 g of water.

The dish is hermetically sealed, then stirred in a shaking machine for 24 hours at ambient temperature.

After 24 hours, the aqueous phase is recovered and weighed. A first aliquot portion of this resulting aqueous phase is recovered and observed with a phase contrast microscope. A second aliquot portion of this aqueous phase is lyophilized and then taken up in a solvent (chloroform).

The dosage of the vesicular lipids (V) and cholesterol or phytosterol is effected by high performance thin layer chromatography (HPTLC) after carbonization, the reading of the plates being made on a Shimadzu densitometer. The dosage of the α-tocopherol acetate is made by high pressure liquid chromatography (HPLC).

The results are given in Table I, below.

TABLE 1

| Composition | Amount of lipid (V) | Amount of cholesterol or phytosterol* | Weight ratio (V)/cholesterol or phytosterol (%) | Amount of α-tocopherol in % | Result of microscope examination |
|---|---|---|---|---|---|
| A** | 0 | 0 | — | 0 | no vesicles |
| A1* | 0 | 0 | — | 0 | no vesicles |
| A2 | 5% | 5% | 50/50 | 0 | numerous vesicles |
| A3 | 6% | 6% | 50/50 | 1.5 | numerous vesicles |
| A4 | 8% | 8% | 60/40 | 0 | vesicles |
| A5 | 8% | 6% | 60/40 | 3 | vesicles |

*dosed relative to the initial amount deposited in the Petri dish
**not part of the invention The results given above show that when the fatty phase of an anhydrous cosmetic composition is added to a provesicular lipidic phase, it is possible, on contact with an aqueous phase, to release, in this aqueous phase, vesicles having the same composition as the provesicular lipidic phase added and that, if there is introduced into the composition a liposoluble active material, the latter is also released in the aqueous phase with the vesicles formed. The mere mixing of the liposoluble active material with the fatty phase does not release the α-tocopherol in the aqueous phase.

The chromatography dosage techniques employed in this example are as follows:

HPTLC dosage technique.

On a 60 Merck silica gel plate without fluorescence indicator, 20 μl of the sample or standard are deposited. The standardization range is effected from 0.5 mg/ml to 3 mg/ml. Migration is made in a vertical tank with an 80/20 chloroform/methanol mixture. Detection is made by pulverization with HSO at 20% in water, then carbonization at 170° C. for 5 minutes. The reading is made on a Shimadzu densitometer at:

400 nm for cholesterol,
470 nm for the nonionic amphiphilic lipid of formula (V) and the oxyethylenated phytosterol (GENEROL 122 E5), and
530 nm for hydrogenated lecithin, sold under the trade name "LECINOL S10" by Nikko.

HPLC dosage technique of α-tocopherol acetate.

| Column | type RP 18 (5 μm) Lichrosorb quality sold by Merck |
|---|---|
| Eluant | pure methanol |
| Flow rate | 1.5 ml/mm |
| λ | 280 nm |
| Injection | 10 μl |

The standards and samples are in solution in chloroform.

EXAMPLE 2

Comparison

Composition Prepared Starting with a Lip Rouge Fatty Phase (1) Preparation of the Compositions As in Example 1 a base B is prepared having the following composition:

| Polybutylene | 5.04 g |
|---|---|
| Lanolin oil | 20.38 g |
| Octoxy glyceryl behenate | 20.38 g |
| Stearylheptanoate | 9.84 g |
| Jojoba oil | 9.84 g |
| Ricin oil | 19.20 g |
| Butylhydroxytoluene | 0.06 g |
| Butylhydroxyanisole | 0.06 g | and to which are added, so as to obtain fatty phases, various amounts, set forth in Table II below, of polyethylene wax, sold under the trade name "POLYWAX 500" by Bareco, and microcrystalline wax.

To the resulting fatty phases two provesicular lipidic phases are added.

Provesicular lipidic phase (1) has the following composition:

| nonionic lipid of formula (V) described in Example 1 | 47.5 g |
|---|---|
| cholesterol | 47.5 g |
| dicetylphosphate | 5.0 g |

Provesicular lipidic phase (2) has the following composition:

| "LECINOL S10" | 60.0 g |
|---|---|
| cholesterol | 30.0 g |
| palmitoylcollagenic acid, sold by Rhone-Poulenc under the trade name "LIPACIDE PCO" | 10.0 g |

The two provesicular lipidic phases are prepared by comelting the components at 100° C. under nitrogen.

Optionally glycerine, which is a water-soluble active material, is added by premixture with the provesicular phase.

Compositions B1 to B9 are thus obtained, the compositions of which are given in Table II below:

TABLE II

| Compositions | Base B in g | Microcrystalline wax in g | Polyethylene wax in g | Glycerine in g | Mixture wt for wt of glycerine and provesicular lipidic phase (1) in g | Mixture wt for wt of glycerine and provesicular lipidic phase (2) in g |
|---|---|---|---|---|---|---|
| B1* | 78.0 | 8.50 | 8.50 | 5.0 | 0 | 0 |
| B2* | 72.8 | 8.60 | 8.60 | 10.0 | 0 | 0 |
| B3* | 67.7 | 8.65 | 8.65 | 15.0 | 0 | 0 |
| B4 | 73.8 | 8.10 | 8.10 |  | 10.0 | 0 |
| B5 | 65.5 | 7.25 | 7.25 |  | 20.0 | 0 |
| B6 | 54.8 | 7.60 | 7.60 |  | 30.0 | 0 |
| B7 | 73.8 | 8.10 | 8.10 |  | 0 | 10.0 |
| B8 | 65.5 | 7.25 | 7.25 |  | 0 | 20.0 |
| B9 | 54.8 | 7.60 | 7.60 |  | 0 | 30.0 |

*not a part of the invention (2) Comparative Tests

A 1 g film of each of fatty phases B1 to B9 is deposited in a Petri dish, then covered with 10 g of water. The dish is hermetically sealed and then agitated on a shaker machine for 24 hours at ambient temperature. After 24 hours the aqueous phase is recovered and weighed.

Dosage of the glycerine is effected enzymatically using the Kit Sigma 337 A.

The results are given in Table III, below

TABLE III

| Composition | Amount of glycerine dosed in the aqueous phase, in % of the initial amount | Potentialization (1) |
|---|---|---|
| B1* | 8 |  |
| B2* | 10 |  |
| B3* | 7 |  |
| B4 | 43 | B4/B1: X5.4 |
| B5 | 59 | B5/B2: X5.9 |
| B6 | 86 | B6/B3: X12.3 |
| B7 | 20 | B7/B1: X2.5 |
| B8 | 31 | B8/B2: X3.1 |
| B9 | 42 | B9/B3: X6 |

*Not part of the invention
(1) Potentialization is the increase factor of the amount of active material released in the water relative to compositions not containing the provesicular lipidic phase.

The results achieved in this example show that the invention potentializes the release of the glycerine in an aqueous environment, whatever the nature of the provesicular lipidic phase employed and the glycerine concentration in this phase.

The dosage of the glycerine according to the Sigma protocol of the Kit No. 337 is effected using the reagent defined below according to the reactions:

Glycerol+ATP $\underrightarrow{GK}$ G-I-P+ADD

G-I-P+$O_2$ $\underrightarrow{GPO}$ DAP+$H_2O_2$ $H_2O_2$+4AAP+ESPA $\underrightarrow{PDA}$ colored quinoneimine+$H_2O$ ATP—Adenosine Triphosphate
GK—Glycerol Kinase
GIP—Glycerol 1 phosphate
ADP—Adenosine 5'-diphosphate
GPO—Glycerol phosphate oxydase
DAP—Dihydroxyacetone phosphate
4-AAP—4 aminoantipyrine
ESPA—Sodium N-ethyl-N (3-sulfopropyl)m-anisidine
POD—Peroxydase The reading is made at 540 nm.
The reagent employed has the following composition:

| | |
|---|---|
| ATP | 0.375 mmol/l |
| Magnesium salt | 3.75 mmol/l |
| Sodium N-ethyl-N-(3-sulfopropyl) m-anisidine | 2.11 mmol/l |
| Glycerol kinase | 1.250 U/l |
| Glycerol phosphate oxydase | 2500 U/l |
| Peroxydase | 2500 U/l |
| Buffer | pH 7 |

As a comparison, the dosage of a blank and various samples is effected in the following proportions:

| | Blank | Sample |
|---|---|---|
| Reagent | 3 ml | 3 ml |
| Sample | — | 0.01 ml |
| Water | 0.01 ml | — |

The calculation of the concentration is made relative to the optical density of a known standard.

EXAMPLE 3

Comparison

Complexion Foundation Released From Ionic Liposomes Charged with Glycerine or Sorbitol (1) Preparation The fatty phase C having the composition given below is produced by mixing waxes and oils at 80° C. with stirring until a homogeneous mixture is obtained. The pigments and fillers are added always at 80° C. and with stirring until a homogeneous color is obtained. The remainder of the components are added and the temperature is maintained at 80° C. for 2 hours with stirring.

The resulting fatty phase C has the following composition:

| | |
|---|---|
| Microcrystalline wax | 4 g |
| Carnauba wax | 6 g |
| Octyl palmitate | 14 g |

-continued

| | |
|---|---|
| Hydrogenated polyisobutane | 17.6 g |
| Trilaurin | 7 g |
| Propyl paraben | 0.1 g |
| Iron oxide (yellow) | 4.9 g |
| Iron oxide (brown-yellow) | 1.9 g |
| Titanium dioxide | 16.5 g |
| Iron oxide (black) | 0.7 g |
| Zinc oxide | 3.0 g |
| Benzophenone-3 | 0.5 g |
| Octyl methoxycinnamate | 0.5 g |
| Dimethicone, sold under the trade name "SILBIONE 70047 V300" by Rhone Poulenc | 0.3 g |
| Nylon, sold under the trade name "L'ORGASOL 2002 Natural EXTRA COS" by Ato | 8.0 g |
| Mica | 15.0 g |

Starting with this fatty phase C, the below compositions are produced, on mixture, in various amounts, of glycerine or sorbitol with a provesicular lipidic phase consisting of a mixture of "LECINOL S10" and an oxyethylenated phytosterol (GENEROL 122 ES), in a 60/40 weight proportion, at a temperature of 80° C. with stirring for 1 hour.

| Composition | Fatty phase C in G | Glycerine in g | Sorbitol in g | LECINOL S10/ phytosterol 60/40 in g |
|---|---|---|---|---|
| C1 | 100 | — | — | — |
| C2 | 95 | 5 | — | — |
| C3 | 95 | — | — | 5 |
| C4 | 90 | 5 | — | 5 |
| C5 | 95 | — | 5 | — |
| C6 | 90 | — | 5 | 5 |

(2) Tests

These compositions were tested in accordance with the method employed in Example 1:

Operating Procedure:

A 1 g film of each of the bases C1 to C6 is deposited in a Petri dish and then covered with 10 g of water.

The dish is hermetically sealed and then stirred on a shaker machine for 24 hours at ambient temperature. After 24 hours, the aqueous phase is recovered and quantified. Dosage of the lipids is made by HPTLC, the glycerine is dosed enzymatically as described above, and the sorbitol is dosed enzymatically in accordance with the following method.

Dosage Method of the Sorbitol

The method is based on the following reaction:

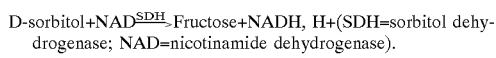

D-sorbitol+NAD $\xrightarrow{SDH}$ Fructose+NADH, H+(SDH=sorbitol dehydrogenase; NAD=nicotinamide dehydrogenase).

Under the test conditions, the reaction is completely displaced to the right. The amount of NADH, H+ formed in the reaction is stoichiometric with the amount of sorbitol; it is determined by measuring the absorbance increase at 340 nm.

Reagents—Preparation of the Solutions

Solution 1: pyrophosphate 0.2 M, pH=9.5 Dissolve 8.92 g of $Na_4P_2O_7 \cdot 10H_2O$ in 80 ml of distilled water. Adjust to pH 9.5 with 1N HCl then to a volume of 100 ml with distilled water.

Solution 2: Dissolve 40 mg of NAD in 2 ml of distilled water.

Solution 3: Sorbitol dehydrogenase (SDH) Dissolve 2 mg in 500 µl of distilled water.

Operating Method

The following solutions are prepared:

| | Blank | Sample |
|---|---|---|
| Solution 1 | 1.00 ml | 1.00 ml |
| Solution 2 | 0.10 ml | 0.10 ml |
| Sample | — | 0.20 ml |
| Distilled water | 1.70 ml | 1.50 ml |

The reaction is started by adding in each tank 0.05 ml of solution 3. The contents are mixed and the optical densities are read after 60 minutes against distilled water at 0.412 λ. Abs., –λ Abs. being the absorbance of the sample less the absorbance of the blank.

The results obtained with the complexion foundation compositions tested are as follows:

TABLE IV

| Formulation | Amount of lipids** | Weight ratio LECINOL S10/phytosterol | Amount of active material in the aqueous phase** | Potentialization |
|---|---|---|---|---|
| C1* | — | — | — | — |
| C2* | — | — | 12 | — |
| C3* | 7 | 60/40 | — | — |
| C4 | 6 | 60/40 | 78 | C4/C2: X6.5 |
| C5* | — | — | 8 | — |
| C6 | 6 | 60/40 | 49 | C6/C5: X6.1 |

*not part of the invention
**dosed relative to the initial amount (%)

The above results show that in the presence of a provesicular lipidic phase, vesicles having the same composition as the lipidic phase are released by mere contact with an aqueous environment. On the other hand, it is shown that the formed vesicles potentialize the release of water-soluble active materials.

EXAMPLE 4

Preparation of a "Two Way Cake"

A binder L having the following composition is prepared:

| | |
|---|---|
| Petrolatum oil | 56.5 g |
| Ricin oil | 10.8 g |
| Petrolatum | 10.0 g |
| Isopropyl myristate | 7.2 g |
| Oleic alcohol | 10.0 g |
| Lanolin | 5.5 g |

There is also prepared, by comelting at 100° C. under nitrogen, a provesicular lipidic phase (3) having the following composition:

| | |
|---|---|
| Nonionic amphiphilic lipid of formula (V) of Example 1 | 47.5 g |
| Cholesterol | 47.5 g |
| Dicetyl phosphate | 5.0 g |

The fillers, pigments and powders are then added until a homogeneous mixture is obtained. The binder and the provesicular lipidic phase previously heated to bring them to the liquid state are added. The whole is then ground together in order to obtain a homogenous composition.

The "two way cake" obtained has the follows composition:

| | |
|---|---|
| Talc, sufficient amount for | 100.0 g |
| Mica | 20.0 g |
| Titanium oxide | 5.0 g |
| Zinc stearate | 2.0 g |
| Nylon powder | 5.0 g |
| Iron oxide | 2.0 g |
| Octyl dimethyl paraaminobenzoate | 0.5 g |
| Perfume | 0.2 g |
| Preservative | 1.0 g |
| Binder L | 8.0 q |
| Provesicular lipidic phase (3) | 2.0 g |
| Glycerine | 2.0 g |
| Vitamin E | 0.1 g |

This composition is applied to the face by the user with a wet sponge.

We claim:

1. An anhydrous cosmetic composition comprising:

a) a lipophilic material mixture comprising a liquid selected from the group consisting of hydrocarbon oils, fatty acid esters, fatty alcohols and mixtures thereof, and a solid selected from the group consisting of fatty alcohols, fatty acid esters, waxes and mixtures thereof;

b) a hydrophilic active material;

c) optionally, a colorant; and d) at least one amphiphilic lipid selected from the group consisting of:

(1) a linear or branched polyglycerolated derivative having the formula

  (II)

wherein
—$C_3H_5(OH)O$— represents the following structures taken in admixture or separately:

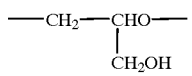

and

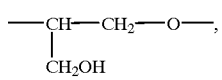

$\overline{n}$ has a statistical average value ranging from 1 to 6, $R_3$ represents:

(a) a linear or branched, saturated or unsaturated aliphatic chain containing from 12 to 30 carbon atoms, or a hydrocarbon radical of a lanolin alcohol, (b) $R_4CO$ wherein $R_4$ is a linear or branched $C_{11}$–$C_{29}$ aliphatic radical, or (c) $R_5$—[—$OC_2H_3(R_6)$—]— wherein $R_5$ has the meaning (a) or (b) of $R_3$; —$OHC_2H_3(R_6)$— represents the following structures taken in admixture or separately:

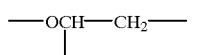

and

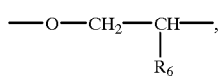

wherein $R_6$ has the meaning (a) for $R_3$;

(2) a linear or branched polyglycerol ether having two fatty chains;

(3) a polyoxyethylenated fatty alcohol;

(4) a polyoxyethylenated sterol or phytosterol;

(5) a polyol ether;

(6) a polyol ester oxyethylenated or not;

(7) a natural or synthetic glycolipid;

(8) a polyglycerolated α-diol;

(9) a hydroxyamide having the formula

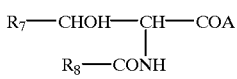

wherein
$R_7$ represents a $C_7$–$C_{21}$ alkyl or alkenyl radical,
$R_8$ represents a saturated or unsaturated $C_7$–$C_{31}$ hydrocarbon radical,
—COA represents a group selected from (i)

wherein B is an alkyl radical derived from a primary or secondary, mono or polyhydroxylated amine, and $R_9$ represents hydrogen, methyl, ethyl and hydroxyethyl, or (ii) —COOZ wherein Z represents the residue of a $C_3$–$C_7$ polyol, (10) an ether or ester having the formula

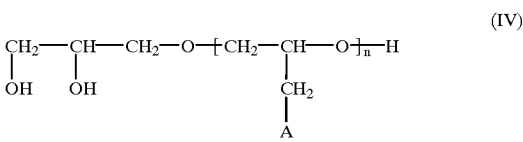  (IV)

wherein
A represents —OR or

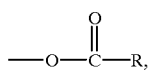

wherein R represents a saturated or unsaturated hydrocarbon radical and $\overline{n}$ has a value of 2 or is a statistical average value n greater than 1 and at most equal to 6,

(11) a natural or synthetic phospholipid, and

(12) an ionic amphiphilic lipid having the formula

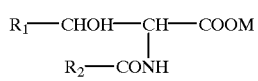

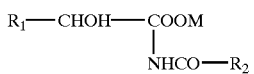

wherein
$R_1$ represents a $C_7$–$C_{21}$ alkyl or alkenyl radical,
$R_2$ represents a saturated or unsaturated $C_7$–$C_{31}$ hydrocarbon radical and M represents H, Na, K, $NH_4$ or an ammonium ion derived from an amine.

2. An anhydrous cosmetic composition of claim 1 wherein said solid is selected from the group consisting of microcrystalline waxes, paraffin waxes, petrolatum waxes, ozokerite, montan wax, beeswax, spermaceti, lanolin wax, lanolin alcohols, hydrogenated lanolin, hydroxylated lanolin, acetylated lanolin, lanolin fatty acids, acetylated lanolin alcohol, candelilla wax, Carnauba wax, Japan wax, hydrogenated ricin oil, hydrogenated palm oil, hydrogenated tallow, and hydrogenated cocoa oil, propylene glycol monomyristate and myristyl myristate, cetyl alcohol, stearyl alcohol, mono-, di- and triglycerides solid at 25° C., stearic monoethanol amide, colophane, glycol adiebates, glycerol abietates, sucroglycerides, oleates of calcium, magnesium, zinc or aluminum, myristates of calcium, magnesium, zinc or aluminum, lanolates of calcium, magnesium, zinc or aluminum, stearates of calcium, magnesium, zinc or aluminum, dihydroxystearates of calcium, magnesium, zinc or aluminium and polyethylene wax, and said liquid is selected from the group consisting of cocoa butter, paraffin oil, petrolatum oil, oils having a boiling point between 310 and 410° C., perhydrosqualene, sweet almond oil, calophyllum oil, palm oil, avocado oil, jojoba oil, olive oil, ricin oil, cereal germ oils, dimethylpolysiloxane oil, purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate, di-isopropyl adipate, oleic alcohol, linoleic alcohol, lanolenic alcohol, isostearyl alcohol, octyl dodecanol, isopropyl lanolate, isocetyl lanolate, acetyl glycerides, octanoates of alcohols, octanoates of polyalcohols, decanoates of alcohols, decanoates of polyalcohols, ricinoleates of alcohols, ricinoleates of polyalcohol, polybutylene, lanolin oil, octoxy glyceryl behenate, stearyl heptanoate, octyl palmitate, hydrogenated polyisobutane, trilaurin and dimethicone.

3. An anhydrous cosmetic composition of claim 1 in the form of a stick.

4. An anhydrous cosmetic composition of claim 1 in the form of a lip rouge.

5. An anhyrous cosmetic composition of claim 1 in the form of a lipstick.

6. An anhydrous cosmetic composition of claim 1 wherein said hydrophilic active material is selected from the group consisting of glycerin, sorbitol, an amino acid, a vitamin and a sunscreen agent.

7. An anhydrous cosmetic composition of claim 6 wherein said hydrophilic active material is glycerin.

8. An anhydrous cosmetic composition of claim 1 wherein said amphiphilic lipid is present in an amount of from 0.1 to 30 percent by weight of the anhydrous composition.

9. An anhydrous cosmetic composition of claim 8 wherein said amphiphilic lipid is present in an amount of from 1 to 20 percent by weight of the anhydrous composition.

10. An anhydrous cosmetic composition of claim 1 wherein said liquid is present in said lipophilic material mixture in an amount of from 35 to 47 percent by weight of said anhydrous composition and said solid is present in said lipophilic material mixture in an amount of from 35 to 43 percent by weight of said anhydrous composition.

11. An anhydrous cosmetic composition of claim 10 in the form of a lip rouge.

12. An anhydrous cosmetic composition of claim 10 in the form of a lipstick.

13. An anhydrous cosmetic composition of claim 1 wherein said hydrophilic active material is present in an amount of from 5 to 15 percent by weight of said anhydrous composition.

14. An anhydrous cosmetic composition of claim 10 wherein said hydrophilic active material is present in an amount of from 5 to 15 percent by weight of said anhydrous composition.

15. An anhydrous cosmetic composition of claim 1 wherein said amphiphilic lipid is present in an amount of from 3 to 9 percent by weight of said anhydrous composition.

16. An anhydrous cosmetic composition of claim 10 wherein said amphiphilic lipid is present in an amount of from 3 to 9 percent by weight of said anhydrous composition.

17. An anhydrous cosmetic composition of claim 13 wherein said amphiphilic lipid is present in an amount of from 3 to 9 percent by weight of said anhydrous composition.

18. An anhydrous cosmetic composition of claim 14 wherein said amphiphilic lipid is present in an amount of from 3 to 9 percent by weight of said anhydrous composition.

19. An anhydrous cosmetic composition of claim 1 wherein said amphiphilic lipid is present in an amount of from 2 to 7 percent by weight of said anhydrous composition.

20. An anhydrous cosmetic composition of claim 6 wherein said amphiphilic lipid is present in an amount of from 2 to 7 percent by weight of said anhydrous composition.

21. An anhydrous cosmetic composition of claim 10 wherein said amphiphilic lipid is present in an amount of from 2 to 7 percent by weight of said anhydrous composition.

22. An anhydrous cosmetic composition of claim 13 wherein said amphiphilic lipid is present in an amount of from 2 to 7 percent by weight of said anhydrous composition.

23. An anhydrous cosmetic composition of claim 14 wherein said amphiphilic lipid is present in an amount of from 2 to 7 percent by weight of said anhydrous composition.

24. An anhydrous cosmetic composition of claim 10 wherein said amphiphilic lipid is present in an amount of from 3 to 9 percent by weight of said anhydrous composition and said hydrophilic active material is present in an amount of 5–15 percent by weight of said anhydrous composition.

25. An anhydrous cosmetic composition of claim 10 wherein said amphiphilic lipid is present in an amount of from 2 to 7 percent by weight of said anhydrous composition and said hydrophilic active material is present in an amount of 5–15 percent by weight of said anhydrous composition.

26. An anhydrous cosmetic composition of claim 1 wherein said solid present in said lipophilic material mixture contains polyethylene wax.

27. An anhydrous cosmetic composition of claim 13 wherein said solid present in said lipophilic material mixture contains polyethylene wax.

28. An anhydrous cosmetic composition of claim 14 wherein said solid present in said lipophilic material mixture contains polyethylene wax.

29. An anhydrous cosmetic composition of claim 15 wherein said solid present in said lipophilic material mixture contains polyethylene wax.

30. An anhydrous cosmetic composition of claim 16 wherein said solid present in said lipophilic material mixture contains polyethylene wax.

31. An anhydrous cosmetic composition of claim 17 wherein said solid present in said lipophilic material mixture contains polyethylene wax.

32. An anhydrous cosmetic composition of claim 18 wherein said solid present in said lipophilic material mixture contains polyethylene wax.

33. An anhydrous cosmetic composition of claim 19 wherein said solid present in said lipophilic material mixture contains polyethylene wax.

34. An anhydrous cosmetic composition of claim 1 wherein said solid is present in said lipophilic material mixture in an amount of 15 percent by weight of said anhydrous composition.

35. An anhydrous cosmetic composition of claim 34 wherein said hydrophilic active material is present in an amount of 5 percent by weight of said anhydrous composition.

36. An anhydrous cosmetic composition of claim 1 wherein said liquid is present in said lipophilic material mixture in an amount of 29 percent by weight of said anhydrous composition.

37. An anhydrous cosmetic composition of claim 34 wherein said liquid is present in said lipophilic material mixture in an amount of 29 percent by weight of said anhydrous composition.

38. An anhydrous cosmetic composition of claim 35 wherein said liquid is present in said lipophilic material mixture in an amount of 29 percent by weight of said anhydrous composition.

39. An anhydrous cosmetic composition of claim 1 wherein said amphiphilic lipid is present in an amount of 3 percent by weight of said anhydrous composition.

40. An anhydrous cosmetic composition of claim 34 wherein said amphiphilic lipid is present in an amount of 3 percent by weight of said anhydrous composition.

41. An anhydrous cosmetic composition of claim 35 wherein said amphiphilic lipid is present in an amount of 3 percent by weight of said anhydrous composition.

42. An anhydrous cosmetic composition of claim 36 wherein said amphiphilic lipid is present in an amount of 3 percent by weight of said anhydrous composition.

43. An anhydrous cosmetic composition of claim 37 wherein said amphiphilic lipid is present in an amount of 3 percent by weight of said anhydrous composition.

44. An anhydrous cosmetic composition of claim 38 wherein said amphiphilic lipid is present in an amount of 3 percent by weight of said anhydrous composition.

45. An anhydrous cosmetic composition of claim 1 wherein colorant is present in an amount of 24 percent by weight of said anhydrous composition.

46. An anhydrous cosmetic composition of claim 39 wherein colorant is present in an amount of 24 percent by weight of said anhydrous composition.

47. An anhydrous cosmetic composition of claim 40 wherein colorant is present in an amount of 24 percent by weight of said anhydrous composition.

48. An anhydrous cosmetic composition of claim 41 wherein colorant is present in an amount of 24 percent by weight of said anhydrous composition.

49. An anhydrous cosmetic composition of claim 42 wherein colorant is present in an amount of 24 percent by weight of said anhydrous composition.

50. An anhydrous cosmetic composition of claim 43 wherein colorant is present in an amount of 24 percent by weight of said anhydrous composition.

51. An anhydrous cosmetic composition of claim 44 wherein colorant is present in an amount of 24 percent by weight of said anhydrous composition.

52. An anhydrous cosmetic composition of claim 1 wherein said solid present in said lipophilic material mixture contains carnauba wax.

53. An anhydrous cosmetic composition of claim 39 wherein said solid present in said lipophilic material mixture contains carnauba wax.

54. An anhydrous cosmetic composition of claim 40 wherein said solid present in said lipophilic material mixture contains carnauba wax.

55. An anhydrous cosmetic composition of claim 41 wherein said solid present in said lipophilic material mixture contains carnauba wax.

56. An anhydrous cosmetic composition of claim 42 wherein said solid present in said lipophilic material mixture contains carnauba wax.

57. An anhydrous cosmetic composition of claim 43 wherein said solid present in said lipophilic material mixture contains carnauba wax.

58. An anhydrous cosmetic composition of claim 44 wherein said solid present in said lipophilic material mixture contains carnauba wax.

59. An anhydrous cosmetic composition of claim 45 wherein said solid present in said lipophilic material mixture contains carnauba wax.

60. An anhydrous cosmetic composition of claim 1 wherein said amphiphlic lipid is a phospholipid.

61. An anhydrous cosmetic composition of claim 1 wherein the liquid is a hydrocarbon oil comprising mineral oils, oils of animal origin, palm oil and mixtures thereof.

62. An anhydrous cosmetic composition of claim 1 wherein the hydrocarbon oil comprises vegetable oils selected from the group consisting of sweet almond oil, avocado oil, jojoba oil, olive oil, ricin oil, cereal germ oils, and mixtures thereof.

63. An anhydrous cosmetic composition of claim 1 wherein the hydrocarbon oil is a mineral oil or a lanoline oil.

64. An anhydrous cosmetic composition of claim 1 wherein the liquid is a fatty alcohol selected from the group consisting of oleic alcohol, linoleic alcohol, lanolenic alcohol, isostearyl alcohol, octyl dodecanol, and mixtures thereof.

65. An anhydrous cosmetic composition of claim 1 wherein the liquid is a fatty acid ester selected from the group consisting of cetyl ricinoleate, isopropyl lanolate, isopropyl myristate, isopropyl palmitate, and mixtures thereof.

66. An anhydrous cosmetic composition of claim 1 wherein the fatty alcohols are solid and selected from the group consisting of cetyl, and stearyl, fatty alcohols and mixtures thereof.

67. An anhydrous cosmetic composition of claim 1 wherein the solid is myristyl myristate.

68. An anhydrous cosmetic composition of claim 1 wherein the liquid is present in said lipophilic material mixture in an amount of 35–47 percent by weight of said anhydrous composition and said solid is present in an amount of 35 to 43 percent by weight of said anhydrous composition, and said composition is in the form of a cosmetic for application to lips.

69. An anhydrous cosmetic composition of claim 1 wherein the solid is a wax selected from the group consisting of candelilla, beeswax, carnauba, spermaceti, montan, ozokerite, paraffin, synthetic waxes, microcrystalline waxes and mixtures thereof.

70. An anhydrous cosmetic composition of claim 1 wherein the active material is a moisturizer.

71. An anhydrous cosmetic composition of claim 70 wherein said moisturizer is selected from the group consisting of glycerine, panthenol, sorbitol, and mixtures thereof.

72. An anhydrous cosmetic composition of claim 71 wherein said moisturizer is glycerin.

73. An anhydrous cosmetic composition of claim 1 additionally comprising skin conditioning agents, stabilizers, preservatives, and mixtures thereof.

74. A process for making an anhydrous composition of claim 1 comprising the steps of:
 a. combine the lipophilic materials in a vessel equipped for heating and mixing;
 b. heat the lipophilic materials and, optionally, a colorant, and mix until a homogeneous melt forms;
 c. combine the amphiphilic lipid and polar solvent in a second vessel equipped for heating and mixing;
 d. heat the mixture from (c) and mix until a melt forms;
 e. homogenize the melt in (d) and add to the mixture of (b);
 f. heat the mixture of (e) and mix until a homogeneous melt forms;
 g. cool the melt of (f) until a solid forms.

75. An anhydrous moisturizing cosmetic composition essentially free of water comprising:
 a. from 44% to 90% lipophilic materials wherein 50% to 65% is a liquid selected from the group consisting of hydrocarbon oils, fatty acid esters, fatty alcohols and mixtures thereof, from 35% to 50% is a solid selected from the group consisting of fatty alcohols, fatty acids esters, waxes having melting points from 55° C. to 110° C., and mixtures thereof;
 b. from 5% to 15% hydrophilic moisturizer dispersed in the lipophilic material(s);
 c. from 0 to 35% of a colorant; and
 d. from 0.1% to 30% of an amphiphilic lipid selected from the group consisting of phospholipids, glyceryl monoalkanoates, glyceryl monoalkenoates, polyglyceryl esters, and mixtures thereof.

76. A cosmetic composition according to claim 75 wherein the liquid is present in said lipophilic materials in an amount of 35–47 percent by weight of said anhydrous composition and said solid is present in an amount of 35 to 43 percent by weight of said anhydrous composition.

77. A cosmetic composition according to claim 76 wherein the liquid is a hydrocarbon oil comprising mineral oils, oils of animal origin, palm oil, and mixtures thereof.

78. A cosmetic composition according to claim 77 wherein the hydrocarbon oil comprises vegetable oils selected from the group consisting of sweet almond oil, calophyllum oil, palm oil, avocado oil, jojoba oil, olive oil, ricin oil, cereal germ oils, and mixtures thereof.

79. A cosmetic composition according to claim 76 wherein the hydrocarbon oil is a mineral oil.

80. A cosmetic composition according to claim 76 wherein the liquid is a fatty alcohol selected from the group consisting of oleic alcohol, linoleic alcohol, lanolenic alcohol, isostearyl alcohol, octyl dodecanol, and mixtures thereof.

81. A cosmetic composition according to claim 76 wherein the liquid is a fatty acid ester selected from the group consisting of cetyl ricinoleate, cetyl acetate, isopropyl lanolate, isopropyl myristate, isopropyl palmitate, and mixtures thereof.

82. A cosmetic composition according to claim 75 wherein the solid is selected from the group consisting of mineral, fossil, animal, synthetic and vegetable waxes, and mixtures thereof.

83. A cosmetic composition according to claim 72 wherein the fatty alcohols are solid and selected from the group consisting of cetyl, and stearyl fatty alcohols and mixtures thereof.

84. A cosmetic composition according to claim 73 wherein the solid is myristyl myristate.

85. A cosmetic composition according to claim 82 wherein the solid is a wax selected from the group consisting of candelilla, beeswax, ozokerite, carnauba, polyethylene wax, and mixtures thereof.

86. A cosmetic composition according to claim 82 wherein the solid is a wax selected from the group consisting of candelilla, beeswax, carnauba, spermaceti, montan, ozokerite, paraffin, beeswax, synthetic waxes, microcrystalline waxes and mixtures thereof.

87. A cosmetic composition according to claim 82 comprising from 14.5% to 15.2% wax selected from the group consisting of microcrystalline wax, polyethylene wax, and mixtures thereof.

88. A cosmetic composition according to claim 75 wherein the moisturizer is selected from the group consisting of glycerine, panthenol, sorbitol, and mixtures thereof.

89. A cosmetic composition according to claim 88 comprising from 10% to 15% of a hydrophilic moisturizer.

90. A cosmetic composition according to claim 89 comprising from 10% to 15% glycerin.

91. A cosmetic composition according to claim 89 comprising 10% hydrophilic moisturizer.

92. A cosmetic composition according to claim 75 comprising from 3% to 9% amphiphilic lipid.

93. A cosmetic composition according to claim 75 additionally comprising skin conditioning agents, stabilizers, preservatives, and mixtures thereof.

94. A cosmetic composition according to claim 75 in the form of a cosmetic for application to lips.

95. A cosmetic composition according to claim 75 wherein the lipophilic materials are present in an amount of from 70% to 80% wherein said liquid is present in said lipophilic materials in an amount of 50% to 53% by weight of said anhydrous composition and said solid is present in an amount of 47 to 50 percent by weight of said anhydrous composition and said amphiphilic lipid is present in an amount of from 5% to 7% by weight of said anhydrous composition.

96. An anhydrous cosmetic composition of claim 1 wherein colorant is present in an amount of 35 percent by weight of said anhydrous composition.

97. An anhydrous cosmetic composition of claim 39 wherein colorant is present in an amount of 35 percent by weight of said anhydrous composition.

98. An anhydrous cosmetic composition of claim 40 wherein colorant is present in an amount of 35 percent by weight of said anhydrous composition.

99. An anhydrous cosmetic composition of claim 41 wherein colorant is present in an amount of 35 percent by weight of said anhydrous composition.

100. An anhydrous cosmetic composition of claim 42 wherein colorant is present in an amount of 35 percent by weight of said anhydrous composition.

101. An anhydrous cosmetic composition of claim 43 wherein colorant is present in an amount of 35 percent by weight of said anhydrous composition.

102. An anhydrous cosmetic composition of claim 44 wherein colorant is present in an amount of 35 percent by weight of said anhydrous composition.

103. An anhydrous cosmetic composition of claim 96 wherein said solid present in said lipophilic material mixture contains carnauba wax.

104. An anhydrous cosmetic composition of claim 76, in the form of a cosmetic for application to lips.

105. An anhydrous cosmetic composition of claim 77, in the form of a cosmetic for application to lips.

106. An anhydrous cosmetic composition of claim 78, in the form of a cosmetic for application to lips.

107. An anhydrous cosmetic composition of claim 79, in the form of a cosmetic for application to lips.

108. An anhydrous cosmetic composition of claim 80, in the form of a cosmetic for application to lips.

109. An anhydrous cosmetic composition of claim 81, in the form of a cosmetic for application to lips.

110. An anhydrous cosmetic composition of claim 82, in the form of a cosmetic for application to lips.

111. An anhydrous cosmetic composition of claim 83, in the form of a cosmetic for application to lips.

112. An anhydrous cosmetic composition of claim 84, in the form of a cosmetic for application to lips.

113. An anhydrous cosmetic composition of claim 85, in the form of a cosmetic for application to lips.

114. An anhydrous cosmetic composition of claim 86, in the form of a cosmetic for application to lips.

115. An anhydrous cosmetic composition of claim 87, in the form of a cosmetic for application to lips.

116. An anhydrous cosmetic composition of claim 88, in the form of a cosmetic for application to lips.

117. An anhydrous cosmetic composition of claim 89, in the form of a cosmetic for application to lips.

118. An anhydrous cosmetic composition of claim 90, in the form of a cosmetic for application to lips.

119. An anhydrous cosmetic composition of claim 91, in the form of a cosmetic for application to lips.

120. An anhydrous cosmetic composition of claim 92, in the form of a cosmetic for application to lips.

121. An anhydrous cosmetic composition of claim 93, in the form of a cosmetic for application to lips.

122. An anhydrous cosmetic composition of claim 1 wherein said amphiphilic lipid is present in a lipidic phase wherein said phase is present in an amount of 5 percent by weight of said composition.

123. An anhydrous cosmetic composition of claim 34 wherein said amphiphilic lipid is present in a lipidic phase wherein said phase is present in an amount of 5 percent by weight of said composition.

124. An anhydrous cosmetic composition of claim 35 wherein said amphiphilic lipid is present in a lipidic phase wherein said phase is present in an amount of 5 percent by weight of said composition.

125. An anhydrous cosmetic composition of claim 36 wherein said amphiphilic lipid is present in a lipidic phase wherein said phase is present in an amount of 5 percent by weight of said composition.

126. An anhydrous cosmetic composition of claim 37 wherein said amphiphilic lipid is present in a lipidic phase wherein said phase is present in an amount of 5 percent by weight of said composition.

127. An anhydrous cosmetic composition of claim 38 wherein said amphiphilic lipid is present in a lipidic phase wherein said phase is present in an amount of 5 percent by weight of said composition.

\* \* \* \* \*